United States Patent
Conyers et al.

(10) Patent No.: US 11,179,558 B2
(45) Date of Patent: *Nov. 23, 2021

(54) BLOOD PUMP CONTROLLERS HAVING DAISY-CHAINED BATTERIES

(71) Applicant: TC1 LLC, St. Paul, MN (US)

(72) Inventors: Kevin Conyers, Pleasant Hill, CA (US); Jesse Gage, Los Altos Hills, CA (US); Carine Hoarau, Lafayette, CA (US); Jaime Arturo Romero, San Leandro, CA (US); Joseph C. Stark, III, San Leandro, CA (US)

(73) Assignee: TC1 LLC, St. Paul, MN (US)

( * ) Notice: Subject to any disclaimer, the term of this patent is extended or adjusted under 35 U.S.C. 154(b) by 272 days.

This patent is subject to a terminal disclaimer.

(21) Appl. No.: 15/980,363

(22) Filed: May 15, 2018

(65) Prior Publication Data
US 2018/0256800 A1    Sep. 13, 2018

Related U.S. Application Data

(63) Continuation of application No. PCT/US2016/062603, filed on Nov. 17, 2016.
(Continued)

(51) Int. Cl.
*A61M 60/871* (2021.01)
*A61M 60/50* (2021.01)
(Continued)

(52) U.S. Cl.
CPC ........ *A61M 60/871* (2021.01); *A61M 60/148* (2021.01); *A61M 60/50* (2021.01);
(Continued)

(58) Field of Classification Search
CPC ...... A61M 1/101; A61M 1/122; A61M 1/127; A61M 1/1086; A61M 60/871;
(Continued)

(56) References Cited

U.S. PATENT DOCUMENTS 3,882,861 A    5/1975 Kettering
4,521,871 A    6/1985 Galdun et al.
(Continued)

FOREIGN PATENT DOCUMENTS

EP      1 812 094 A     5/2006
WO     2006/055745 A2   5/2006
(Continued)

OTHER PUBLICATIONS

My LVAD, "Berlin Heart Incor",Retrieved from Internet:http://www.mylvad.com/content/berlin-heart-incor, Jul. 16, 2015, 3 pages.
(Continued)

*Primary Examiner* — Mallika D Fairchild
(74) *Attorney, Agent, or Firm* — Kilpatrick Townsend & Stockton LLP

(57) ABSTRACT

Systems and related methods for supplying power to an implantable blood pump are provided. A system includes a base module and a plurality of energy storage devices. A first energy storage device is operatively coupled to the base module. A second energy storage device is operatively coupled to the first modular energy storage device. The energy storage devices are mechanically coupled in series, electrically coupled in parallel, and configured to provide redundant sources of power to drive an implantable blood pump.

21 Claims, 9 Drawing Sheets

Related U.S. Application Data

(60) Provisional application No. 62/258,205, filed on Nov. 20, 2015.

(51) Int. Cl.
  *A61M 60/148* (2021.01)
  *A61M 60/205* (2021.01)
  *H02J 7/00* (2006.01)

(52) U.S. Cl.
  CPC .......... *H02J 7/0024* (2013.01); *A61M 60/205* (2021.01); *A61M 2205/8237* (2013.01); *H02J 2007/0067* (2013.01)

(58) Field of Classification Search
  CPC .. A61M 60/50; A61M 60/148; A61M 60/205; H02J 7/0024
  See application file for complete search history.

(56) References Cited

U.S. PATENT DOCUMENTS

| | | |
|---|---|---|
| 5,046,965 A | 9/1991 | Neese et al. |
| 5,695,474 A | 12/1997 | Daugherty |
| 5,888,242 A | 3/1999 | Antaki et al. |
| 5,935,105 A | 8/1999 | Manning et al. |
| 5,991,595 A | 11/1999 | Romano et al. |
| 6,071,093 A | 6/2000 | Hart |
| 6,106,971 A | 8/2000 | Spotnitz |
| 6,116,862 A | 9/2000 | Rau et al. |
| 6,146,179 A | 11/2000 | Denny et al. |
| 6,183,412 B1 | 2/2001 | Benkowski et al. |
| 6,234,772 B1 | 5/2001 | Wampler et al. |
| 6,264,635 B1 | 7/2001 | Wampler et al. |
| 6,494,736 B2 | 12/2002 | Mito et al. |
| 6,592,620 B1 | 7/2003 | Lancisi et al. |
| 6,688,861 B2 | 2/2004 | Wampler |
| 7,340,304 B2 | 3/2008 | MacDonald et al. |
| 7,425,142 B1 | 9/2008 | Putz et al. |
| 7,658,613 B1 | 2/2010 | Griffin et al. |
| 7,699,586 B2 | 4/2010 | Larose et al. |
| 7,961,156 B2 | 6/2011 | Knott et al. |
| 7,976,271 B2 | 7/2011 | Larose et al. |
| 7,997,854 B2 | 8/2011 | Larose et al. |
| 8,007,254 B2 | 8/2011 | Larose et al. |
| 8,029,441 B2 | 10/2011 | Mazza et al. |
| 8,152,493 B2 | 4/2012 | Larose et al. |
| 8,157,720 B2 | 4/2012 | Marseille et al. |
| 8,186,665 B2 | 5/2012 | Akema |
| 8,323,174 B2 | 12/2012 | Jeevanandam et al. |
| 8,344,847 B2 | 1/2013 | Moberg et al. |
| 8,348,678 B2 | 1/2013 | Hardisty et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,628,460 B2 | 1/2014 | Yomtov et al. |
| 8,639,348 B2 | 1/2014 | Geheb |
| 8,652,024 B1 | 2/2014 | Yanai et al. |
| 8,657,733 B2 | 2/2014 | Ayre et al. |
| 8,668,473 B2 | 3/2014 | Larose et al. |
| 8,684,763 B2 | 4/2014 | White et al. |
| 8,894,561 B2 | 11/2014 | Callaway et al. |
| 8,971,958 B2 | 3/2015 | Frikart et al. |
| 9,302,035 B2 | 4/2016 | Flaherty et al. |
| 2002/0007198 A1 | 1/2002 | Haupert et al. |
| 2005/0071001 A1 | 3/2005 | Jarvik |
| 2007/0078293 A1 | 4/2007 | Shambaugh et al. |
| 2007/0142696 A1 | 6/2007 | Crosby et al. |
| 2008/0021394 A1 | 1/2008 | Larose et al. |
| 2009/0118827 A1 | 5/2009 | Sugiura |
| 2009/0203957 A1 | 8/2009 | Larose et al. |
| 2011/0160516 A1* | 6/2011 | Dague ................. A61M 1/1086 600/16 |
| 2011/0218383 A1 | 9/2011 | Broen et al. |
| 2012/0046514 A1 | 2/2012 | Bourque |
| 2012/0095281 A1 | 4/2012 | Reichenbach et al. |
| 2012/0172657 A1 | 7/2012 | Marseille et al. |
| 2012/0183261 A1 | 7/2012 | Schwandt et al. |
| 2013/0053909 A1* | 2/2013 | Elghazzawi ......... A61N 1/3975 607/5 |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0073838 A1 | 3/2014 | Dague et al. |
| 2014/0194985 A1 | 7/2014 | Vadala, Jr. |
| 2014/0243970 A1 | 8/2014 | Yanai |
| 2014/0309733 A1 | 10/2014 | Cotter et al. |
| 2015/0038771 A1 | 2/2015 | Marseille et al. |
| 2015/0120067 A1* | 4/2015 | Wing ................. A61M 16/0051 700/282 |
| 2015/0290374 A1 | 10/2015 | Bourque et al. |
| 2016/0095968 A1 | 4/2016 | Rudser |
| 2018/0250459 A1 | 9/2018 | Kimball et al. |
| 2018/0256796 A1 | 9/2018 | Hansen |
| 2018/0256801 A1 | 9/2018 | Conyers et al. |

FOREIGN PATENT DOCUMENTS

| | | |
|---|---|---|
| WO | 2014107424 A2 | 7/2014 |
| WO | 2017087380 A1 | 5/2017 |
| WO | 2017087728 A1 | 5/2017 |
| WO | 2017087785 A1 | 5/2017 |

OTHER PUBLICATIONS

HeartMate II, "The HeartMate II system", Left Ventricular Assist System, Retrieved from Internet http://heartmateii.com/heartmate-ii-system.aspx, Jul. 16, 2015, 2 pages.

* cited by examiner

BLOOD PUMP CONTROLLERS HAVING DAISY-CHAINED BATTERIES

CROSS-REFERENCE TO RELATED APPLICATION

The present application is a continuation of PCT/US2016/062603 filed Nov. 17, 2016, which claims priority to and benefit of U.S. Provisional Application No. 62/258,205, filed Nov. 20, 2015, the disclosures of which are incorporated herein by reference in their entirety for all purposes.

BACKGROUND

Ventricular assist devices, known as VADs, often include an implantable blood pump and are used for both short-term (i.e., days, months) and long-term applications (i.e., years or a lifetime) when a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

While a VAD can greatly improve the quality of a patient's life, the consequences of insufficient power for proper operation of the VAD are significant to patient safety. All ventricular assist systems (VAS) require several watts of power to provide cardiac support. Thus, patients using a VAS and their supporting caregivers or providers (hereinafter "users") can use non-implanted replenishable and/or replaceable power supplies to maintain mobility. Such non-implanted power supplies typically include battery packs and AC wall power converters. The power from these sources may be conveyed to the VAD via a VAS controller using cables.

Battery packs are often carried by the patient. Existing battery packs, however, are heavy and provide limited options for expanding or contracting the weight of battery packs carried by the patient. Instead, many existing products employ a single energy storage configuration, typically a battery of fixed capacity. While some existing devices allow for an optional larger capacity battery pack to be used in lieu of a standard battery pack, options for tailoring the weight of batteries carried by the patient are limited. For example, a patient may have different battery support needs depending on the patient's activity on a given day, but because existing devices often do not allow patients to select a battery configuration based on such needs, the patient may have to use more battery capacity than necessary or limit their activity. Moreover, because of the criticality of powering VADs described above, there is a need to provide modularity of battery configurations while maintaining redundancy. Merely adding a redundant battery can add undesirable weight, cost, and complications such as confusion when switching batteries.

Accordingly, improved portable energy supply systems and related methods that do not have at least some of the above-discussed disadvantages would provide benefits to users of wearable or implanted medical devices.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments described herein include energy supply systems for wearable or implantable medical devices, and related methods that can provide increased flexibility with regard to carried battery capacity and increased reliability in powering such medical devices. In many embodiments, a plurality of energy storage devices are mechanically coupled in series, and electrically coupled in parallel, and configured to provide redundant sources of power to drive an implantable blood pump. The energy storage devices include additional input connectors to allow additional energy storage devices to be mechanically and electrically coupled thereto. The energy storage devices provide patients increased flexibility to appropriately meet the power capacity needs and avoid burdensome weight that is not otherwise needed for applicable activities.

Thus, in one aspect, a system is provided for supplying power to an implantable blood pump. The system includes a base module and a plurality of energy storage devices. The base module is operatively coupled with the blood pump to supply electrical power to drive the implantable blood pump. The first modular energy storage device is configured to be operatively coupled to the base module to supply electrical power to the base module, and the second modular energy storage device is operatively coupled to the first modular energy storage device to supply electrical power to the first modular energy storage device. The second modular energy storage device is mechanically coupled in series to the first modular energy storage device and electrically coupled in parallel to the first modular energy storage device, and the first and second modular energy storage devices are configured to provide redundant sources of power to drive the implantable blood pump.

In many embodiments of the system, the first and second modular energy storage devices comprise one or more battery cells. In many embodiments of the system, the first modular energy storage device is configured to be releasably coupled to the base module, and the second modular energy storage device is configured to be releasably coupled to the first modular energy storage device.

In many embodiments of the system, the first and second modular energy storage devices include battery cells storing electrical power and connectors to transfer electrical power. In many embodiments of the system, each of the first and second modular energy storage devices includes one or more battery cells configured to store electrical power, an input connector configured to receive electrical power, and an output connector configured to output electrical power. In many embodiments of the system, each of the first and second modular energy storage devices includes first and second input connectors each configured to receive electrical power and an output connector configured to output electrical power.

In many embodiments of the system, the first and second modular energy storage devices and the base module include connectors connectable to transfer electrical power. In many embodiments of the system, a first output connector of the first modular energy storage device is connectable to a base module input connector of the base module and an input connector of the first modular energy storage device is connectable to a second output connector of the second modular energy storage device.

In many embodiments, the system further includes a third modular energy storage device operatively coupled to the second modular energy storage device. In some embodiments, the third modular energy storage device is mechanically coupled in series to the second modular energy storage device and electrically coupled in parallel to the second modular energy storage device, and the third modular energy storage device is configured to provide an additional redundant source of power to drive the implantable blood pump.

In many embodiments of the system, the first and second modular energy storage devices may be similar. For example, the first modular energy storage device and the second modular energy storage device may be configured to be interchangeable. As another example, the first modular energy storage device and the second modular energy storage device may be configured to be substantially identical.

In many embodiments of the system, the base module includes a controller coupled to the implantable blood pump. The controller includes an internal energy storage device configured to provide power to drive the implantable blood pump, and the first or second modular energy storage devices are configured to provide power to drive the implantable blood pump when the internal energy storage device is in a substantially depleted state. In some embodiments, the base module includes a controller that powers the implantable pump through a driveline cable. In some embodiments, the base module includes an external energy transmitter that powers the implantable pump wirelessly by transcutaneous energy transmission.

In many embodiments, the system further includes an alternate power source coupled to an input connector of the second modular energy storage device. For example, the alternate power source may include a charging unit drawing power from a standard AC power outlet. In some embodiments, the charging unit is configured to charge at least one of the modular energy storage devices during operation of the implantable blood pump.

In many embodiments of the system, the components are configured to be worn externally by a patient. In many embodiments of the system, each of the first and second modular energy storage devices and the base module are configured to be worn externally by a patient implanted with the blood pump.

In many embodiments of the system, the base module includes one or more indicators configured to indicate a level of power available to drive the implantable blood pump or a fault associated with the implantable blood pump. For example, the indicators may be visual indicators and/or audio indicators. In some embodiments, the base module is configured to wirelessly transmit one or more notifications regarding the level of power available or the fault to an external device.

In many embodiments of the system, each of the first and second modular energy storage devices includes one or more indicators. For example, in some embodiments of the system, each of the first and second modular energy storage devices includes one or more indicators configured to indicate a remaining power level of the respective modular energy storage device.

In another aspect, a modular external electrical power system is provided for supplying power to an implantable blood pump. The system includes a first modular energy storage device and a second modular energy storage device. The first modular energy storage device is operatively configured to supply electrical power to drive the implantable blood pump, and the second modular energy storage device is releasably coupled to the first modular energy storage device. Each of the first and second modular energy storage devices may include one or more battery cells to store electrical power, an input connector configured to receive electrical power, and an output connector configured to output electrical power. The second modular energy storage device is mechanically coupled in series to the first modular energy storage device and electrically coupled in parallel to the first modular energy storage device, and the first and second modular energy storage devices are configured to provide redundant sources of electrical power to drive the implantable blood pump.

In many embodiments of the system, the first and second modular energy storage devices may have a variety of functions. In some embodiments of the system, each of the first and second modular energy storage devices is a battery module. In some embodiments of the system, the first modular energy storage device is a control unit configured to drive the implantable blood pump and the second modular energy storage device is a battery module.

In many embodiments, the system further includes a third modular energy storage device releasably coupled to the second modular energy storage device. The third modular energy storage device includes one or more battery cells to store electrical power, an input connector configured to receive electrical power, and an output connector configured to output electrical power. The third modular energy storage device is mechanically coupled in series to the second modular energy storage device and electrically coupled in parallel to the second modular energy storage device, and is configured to provide an additional redundant source of electrical power to drive the implantable blood pump.

In many embodiments of the system, the first and second modular energy storage devices are similar. In many embodiments of the system, the first modular energy storage device and the second modular energy storage device are interchangeable. In many embodiments of the system, the first modular energy storage device and the second modular energy storage device are substantially identical.

In many embodiments, the system further includes an alternate power source coupled to the input connector of the second modular energy storage device. For example, the alternate power source may include a charging unit drawing power from a standard AC power outlet. In some embodiments, the charging unit is configured to charge at least one of the modular energy storage devices during operation of the implantable blood pump.

In many embodiments of the system, components are configured to be worn externally by a patient. In many embodiments of the system, the first and second modular energy storage devices are configured to be worn externally by a patient.

In still another aspect, a mechanical circulatory support system is provided. The system includes an implantable blood pump, a controller for driving the implantable blood pump, and a modular energy storage device. The controller includes an internal battery configured to provide power to drive the implantable blood pump. The modular energy storage device is mechanically coupled in series to the controller and electrically coupled in parallel to the controller, and the energy storage device is configured to provide power to drive the implantable blood pump when the internal battery of the controller is in a substantially depleted state.

In many embodiments of the system, additional modular energy storage devices may be coupled to the modular energy storage devices. In some embodiments of the system, the modular energy storage device includes an input connector for receiving electrical power from an additional modular energy storage device, and each of the modular energy storage device and the additional modular energy storage device include one or more battery cells. In some embodiments, the system also includes the additional modular energy storage device. In some embodiments of the system, the additional modular energy storage device may be releasably coupled to the modular energy storage device. In some embodiments of the system, the additional modular energy storage device may be mechanically coupled in series to the modular energy storage device and electrically coupled in parallel to the modular energy storage device. In some embodiments of the system, the additional modular energy storage device includes an additional input connector for receiving electrical power.

In another aspect, a method is provided for electrically powering an implantable blood pump. The method includes connecting a first external energy storage device to a base module operatively configured to supply electrical power to drive the implantable blood pump, and connecting a second external energy storage device to the first energy storage device, wherein the first energy storage device and second energy storage device are mechanically connected in series and electrically connected in parallel. The first and second energy storage devices are configured to provide redundant sources of electrical power to drive the implantable blood pump.

In many embodiments of the method, the base module includes a controller comprising an internal energy storage device. In many embodiments of the method, the first and second energy storage devices are configured to provide electrical power when the internal energy storage device is in a substantially depleted state.

In many embodiments, the method further includes connecting the second external energy storage device to a charging unit drawing power from a standard AC power outlet. In many embodiments of the method, the charging unit is configured to charge at least one of the first external energy storage device or the second external energy storage device during operation of the implantable pump.

In many embodiments of the method, the modular energy storage devices may be disconnected for flexibility. In many embodiments, the method further includes disconnecting the second modular energy storage device when less power capacity is required.

In many embodiments, the method further includes connecting a third external energy storage device to the second energy storage device. In some embodiments, the second energy storage device and the third energy storage device are mechanically connected in series and electrically connected in parallel, and the third energy storage device is configured to provide an additional redundant source of electrical power to drive the implantable blood pump.

In another aspect, a method is provided for electrically powering an implantable blood pump. The method includes supplying power to drive the implantable pump from a base module and supplying power to the base module from at least one of a first or second modular energy storage device. The base module comprises a controller coupled to the implantable blood pump, the controller includes an internal energy storage device configured to provide the power to drive the implantable blood pump, and the first energy storage device and second energy storage device are mechanically connected in series and electrically connected in parallel.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
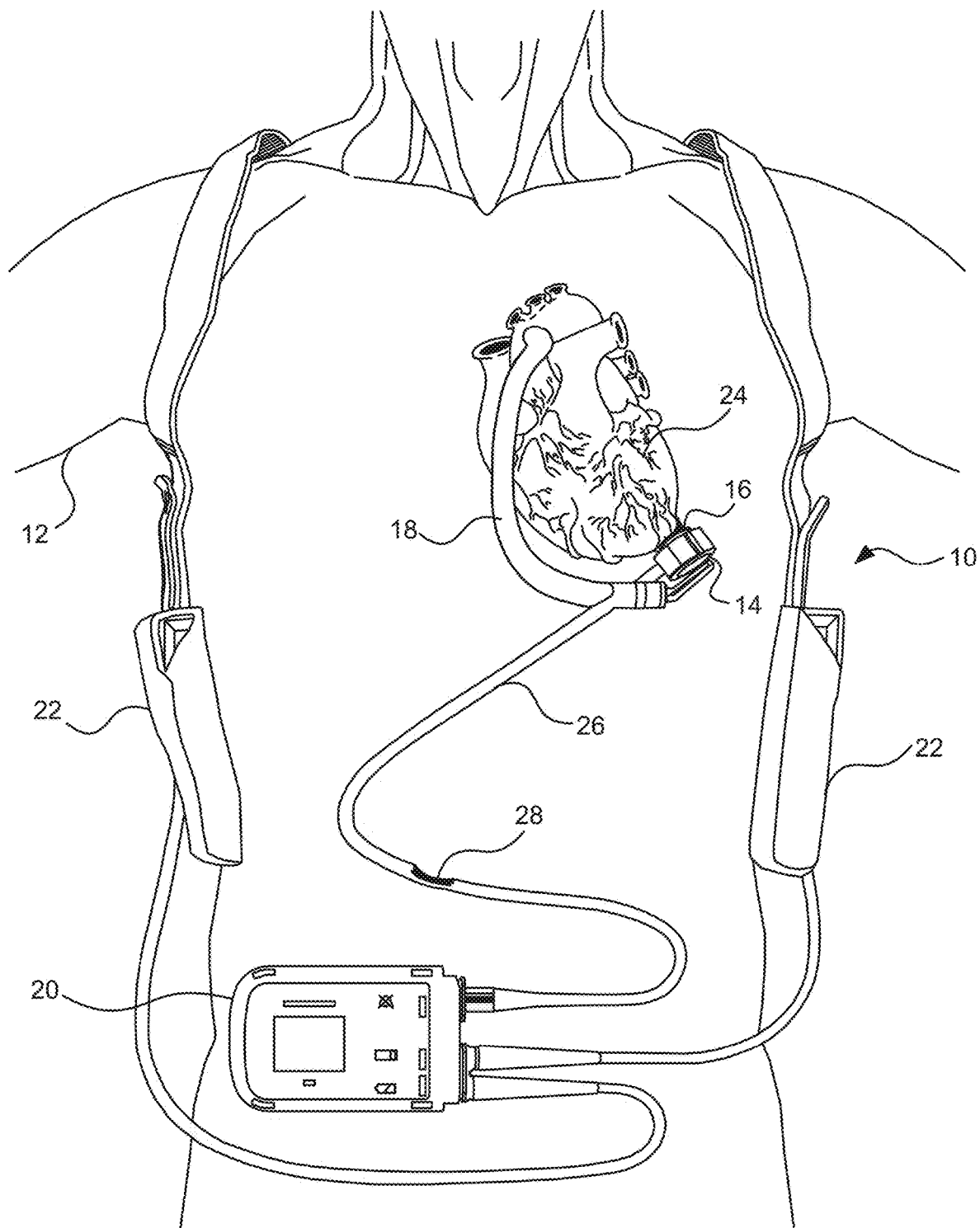
FIG. 1 is an illustration of a mechanical circulatory support system implanted in a patient's body, in accordance with many embodiments.

FIG. 1 is an illustration of a mechanical circulatory support system 10 implanted in a patient's body 12. The mechanical circulatory support system 10 includes an implantable blood pump assembly 14, ventricular cuff 16, outflow cannula 18, an external system controller 20, and power sources 22. The implantable blood pump assembly 14 can include a VAD that is attached to an apex of the left ventricle, as illustrated, or the right ventricle, or both ventricles of the heart 24. The VAD can include a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIG. 1, the blood pump assembly 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 that exits through the patient's abdomen 28, connects the implanted blood pump assembly 14 to the external system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system may be powered by either one, two, or more batteries 22. As can be seen in FIG. 1, batteries 22 are both mechanically connected to the external system controller 20. Batteries 22 are thus both mechanically and electrically connected in parallel. It will be appreciated that although the system controller 20 and power source 22 are illustrated outside/external to the patient body, the driveline 26, system controller 20 and/or power source 22 may be partially or fully implantable within the patient, as separate components or integrated with the blood pump assembly 14. Examples of such modifications are further described in U.S. Pat. No. 8,562,508 and U.S. Patent Publication No. 2013/0127253, all of which are incorporated herein by reference for all purposes in their entirety.

Figure 2:
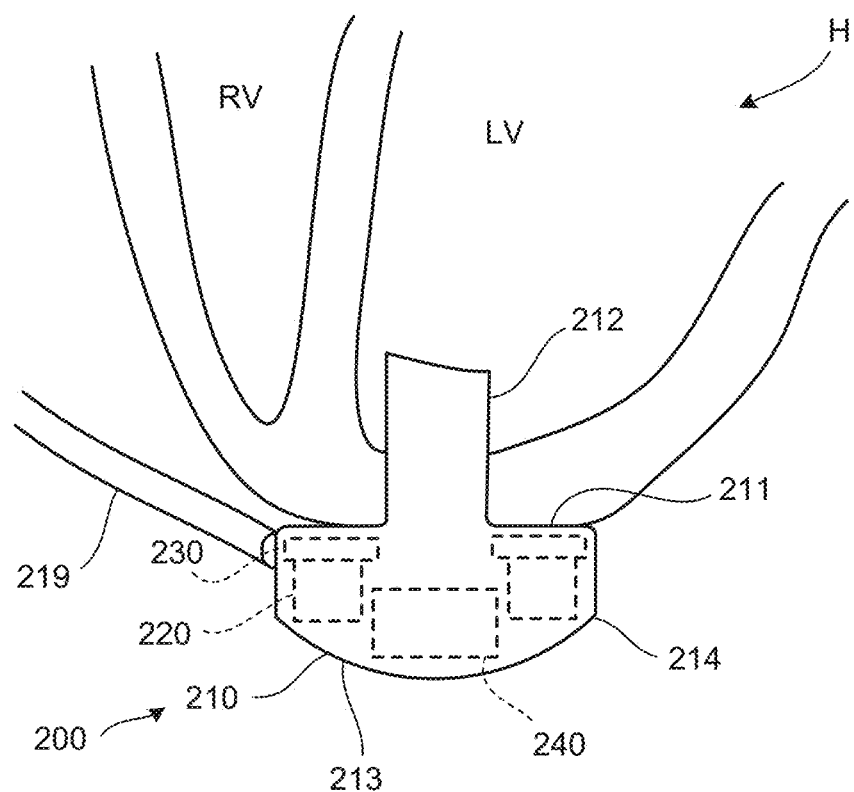
FIG. 2 is an illustration of a blood pump in an operational position implanted in a patient's body, in accordance with many embodiments.

With reference to FIG. 2, a left ventricular assist blood pump assembly 200 (which may correspond with blood pump assembly 14 described above) having a circular shaped housing 210 is implanted in a patient's body with a first face 211 of the housing 210 positioned against the patient's heart H and a second face 213 of the housing 210 facing away from the heart H. The first face 211 of the housing 210 includes an inlet cannula 212 extending into the left ventricle LV of the heart H. The second face 213 of the housing 210 has a chamfered edge 214 to avoid irritating other tissue that may come into contact with the blood pump assembly 200, such as the patient's diaphragm. To construct the illustrated shape of the puck-shaped housing 210 in a compact form, a stator 220 and electronics 230 of the pump assembly 200 are positioned on the inflow side of the housing toward first face 211, and a rotor 240 of the pump assembly 200 is positioned along the second face 213. This positioning of the stator 220, electronics 230, and rotor 240 permits the edge 214 to be chamfered along the contour of the rotor 240, as illustrated in FIG. 2, for example.

Figure 3:
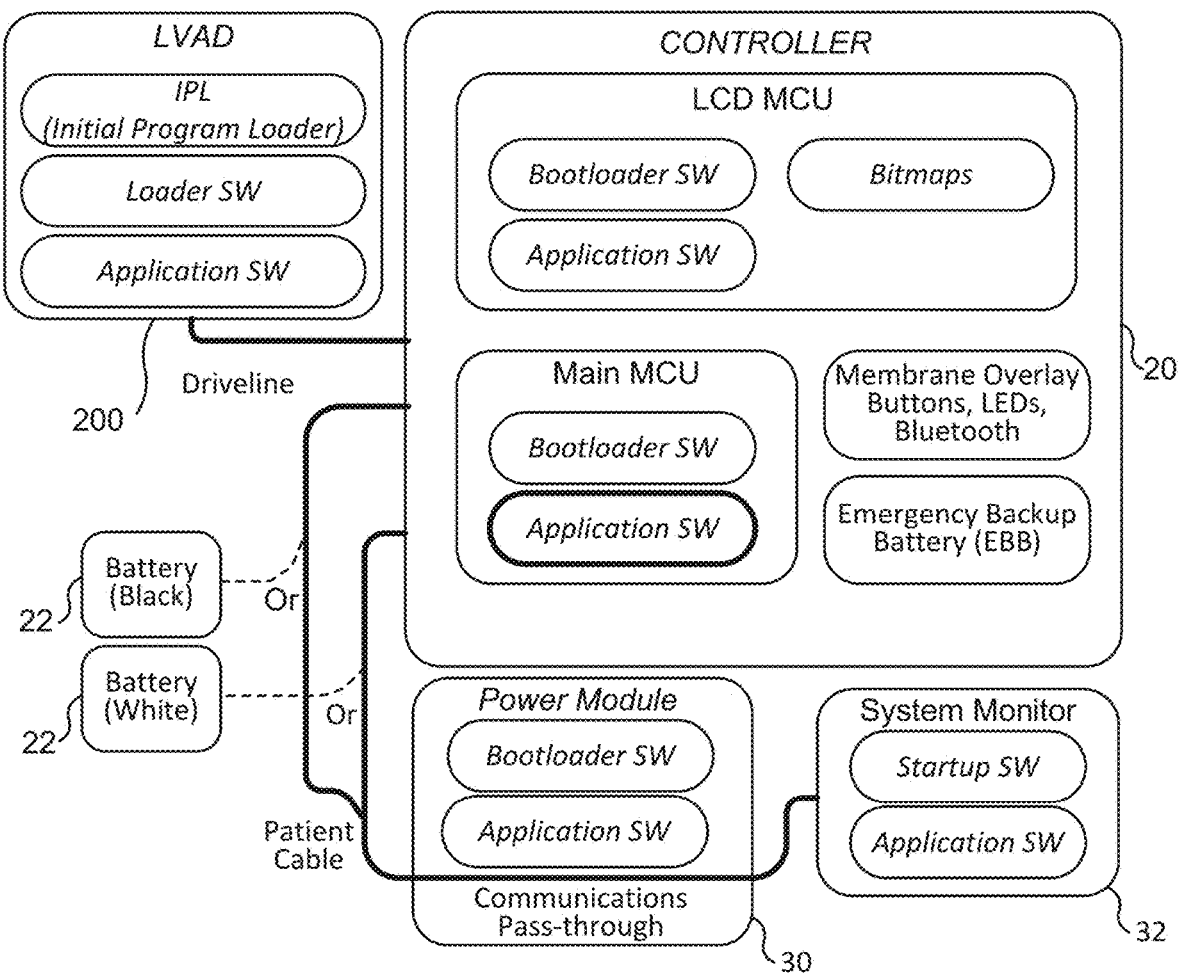
FIG. 3 is a schematic diagram of an overall communication architecture of the mechanical support system of FIG. 1.

FIG. 3 is a schematic diagram of an overall communication architecture of the mechanical support system of FIG. 1. A driveline couples the implanted blood pump assembly 200 to the external system controller 20, which monitors system operation via various software applications. The blood pump assembly 200 itself also includes several software applications that are executable by the on board electronics 230 (e.g., processors) for various functions, such as to control radial levitation and/or drive of the rotor of the pump assembly 200 during operation. The external system controller 20 may in turn be coupled to either batteries 22 or a power module 30 that connects to an AC electrical outlet. The external system controller 20 may also include an emergency backup battery (EBB) to power the system (e.g., when the batteries 22 are depleted) and a membrane overlay, including Bluetooth capabilities for wireless data communication. An external computer having a system monitor 32 that is configurable by an operator, such as clinician or patient, may further be coupled to the circulatory support system for configuring the external system controller 20, implanted blood pump assembly 200, and/or patient specific parameters, updating software on the external system controller 20 and/or implanted blood pump assembly 200, monitoring system operation, and/or as a conduit for system inputs or outputs.

While the mechanical support system described above with respect to FIGS. 1-3 can be powered by a number of different components including batteries 22, an emergency backup battery included in external system controller 20, or power module 30, such systems (and other similarly available mechanical support systems) present a number of limitations. First, since batteries 22 are electrically and mechanically connected in parallel to controller 20 and each battery 22 has only one connection which is used to electrically and mechanically connect it to controller 20, the battery operation shown in FIG. 1 does not provide for easily modifying power capacity to accommodate varying usage. Rather, in such systems, the only way to increase or decrease capacity is to use different capacity batteries in place of batteries 22, which may or may not be available for a given system, and which may not otherwise be feasible for manufacturers to provide due to costs associated therewith. For the same reason, batteries 22 may not be charged while connected to controller 20, which means that an alternate source of power must be used when batteries 22 are being charged, including a different set of batteries or power module 30. In view of these limitations, systems such as system 10 depicted in FIG. 1 typically require batteries 22 that are able to provide power for an extended period of time. Given the capacity needed, such batteries are often heavy, bulky, and burdensome to carry around, and greatly limit the mobility of patients with VADs. Embodiments are described herein with reference to FIGS. 4-10 that address the limitations above and other limitations as will be understood in the following description.

Figure 4:
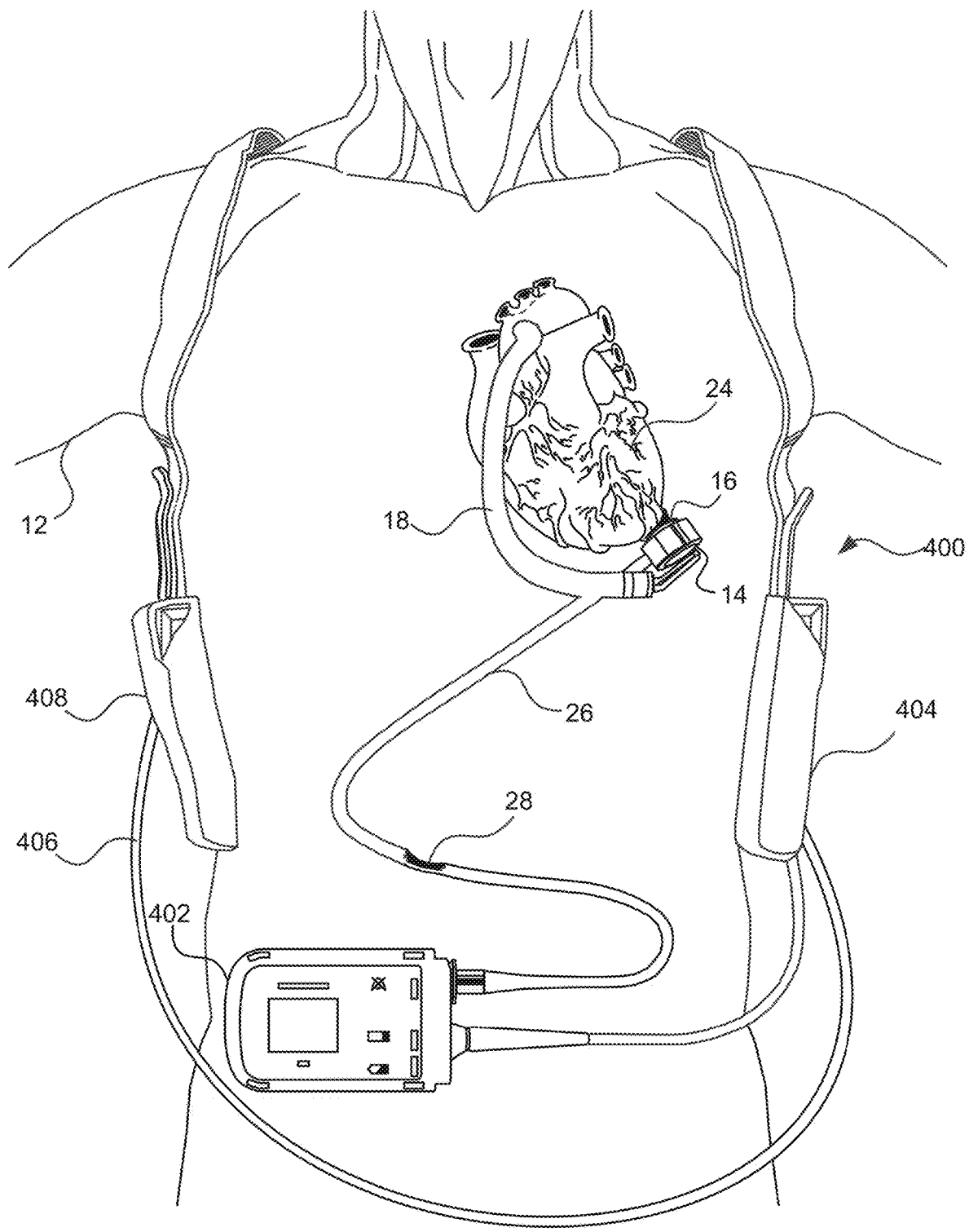
FIG. 4 is an illustration of a mechanical circulatory support system that employs a modular external power supply system, in accordance with many embodiments.

FIG. 4 illustrates a mechanical circulatory support system 400 that employs a modular external power supply system. As with mechanical circulatory support system 10 described above with respect to FIG. 1, mechanical circulatory support system 400 includes an implantable blood pump assembly 14, ventricular cuff 16, outflow cannula 18, and a driveline 26 that exits through the patient's abdomen 28. In mechanical circulatory support system 400, however, the driveline 26 connects the implanted blood pump assembly 14 to a base module 402, which may include a controller that monitors and provides indications regarding system 400 operation, as will be described further herein. The base module 402 can also include battery cells used to power implantable blood pump 14 as will also be discussed in further detail below.

The mechanical circulatory support system 400 further includes batteries 404 and 408. As can be seen in FIG. 4, the battery 404 and the battery 408 are connected mechanically in series, i.e., the battery 404 is connected directly to the base module 402, and the battery 408 is connected to the battery 404 via a coupling 406. As will be described in further detail, while the batteries 404 and 408 can be mechanically coupled in series, they are configured to be electrically coupled in parallel, in accordance with embodiments of the invention. Although not shown in detail, each of the batteries 404, 408 can include two connectors to allow for the serial coupling depicted in FIG. 4. In some embodiments, each of the batteries 404, 408 includes an output connector for providing electrical power to base module 402 and/or implantable blood pump 14 and an input connector to receive electrical power from battery 408 via coupling 406 or from another power source.

Although the coupling 406 is illustratively depicted as a cable connection, it will be understood that this serial connection may be achieved by any suitable coupling, so long as battery 404 is provided with a connector configured to connect to the coupling 406 to the battery 404. For example, batteries 404 and 408 may be connected by connectors that snap or click into place, by pins or lock-pins, by magnetic connectors, by one or more hinges, by ball-and-socket connectors, thrust bearing joints, belts, chains, strings, ropes, nuts and bolts or screws, threads, crush rib or other press fit, crimp connection, adhesive or adhesive tape or Velcro or similar materials, elastic rivet, O-ring and wiper combination, or an over-molding that captures a part.

In many embodiments, the battery 408 includes two connectors, including an output connector configured to provide electrical power to battery 408, base module 402, and/or implantable blood pump 14, via coupling 406 and an input connector to receive electrical power from another power source. For example, although not shown in FIG. 4, the battery 408 can include an input connector to receive electrical power from another battery, a charging unit that draws electrical power from a standard AC power outlet, or any other suitable source of electrical power.

In many embodiments, the batteries 404 and 408 are designed to be interchangeable, so that they may be freely swapped with other interchangeable batteries as they are charged or otherwise replaced. For example, the batteries 404 and 408 can include the same types of connectors, and may have the same form factor so as to each fit in the same wearable holsters or other wearable supports. In some embodiments, the batteries 404 and 408 are substantially identical, so that multiple different batteries need not be manufactured and/or purchased by the user. The batteries 404, 408, however, can have different sizes, shapes, and/or capacities, to allow for increased user flexibility.

Figure 5:
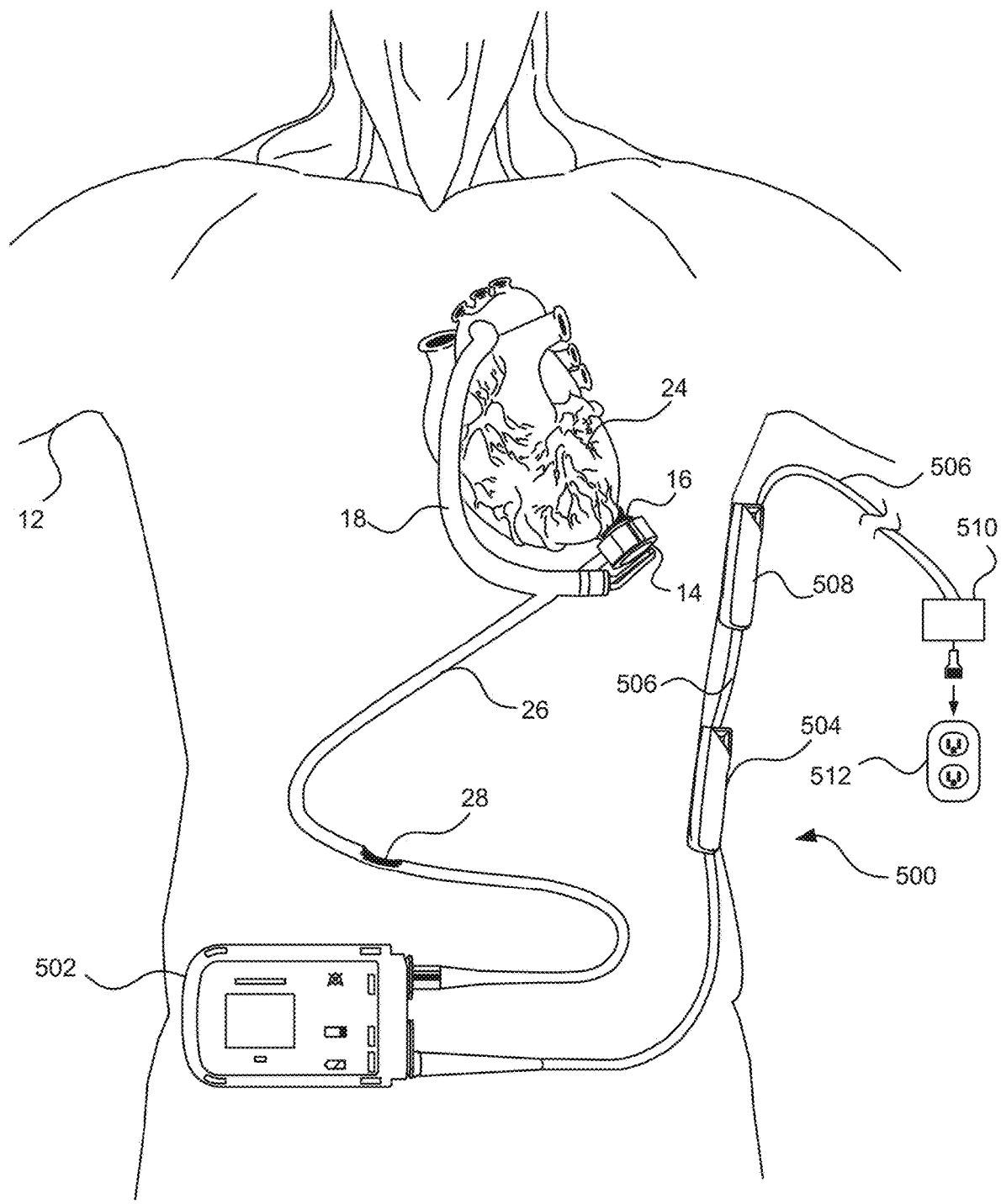
FIG. 5 is an illustration of a mechanical circulatory support system that employs a modular external power supply system, in accordance with many embodiments.

FIG. 5 illustrates a mechanical circulatory support system 500 that employs a modular external power supply system. As with the mechanical circulatory support system 10 and 400 described above with respect to FIGS. 1 and 4, the mechanical circulatory support system 500 includes an implantable blood pump assembly 14, ventricular cuff 16, outflow cannula 18, and a driveline 26 that exits through the patient's abdomen 28. As with the mechanical circulatory support system 400, the mechanical circulatory support system 500 includes a driveline 26 that connects the implanted blood pump assembly 14 to a base module 502.

As with the mechanical circulatory support system 400, the mechanical circulatory support system 500 includes batteries 504, 508 mechanically coupled serially via the coupling 506 and electrically coupled in parallel. The mechanical circulatory support system 500 includes an alternate configuration of batteries 504, 508 relative to the batteries 404, 408 depicted in FIG. 4. Specifically, as seen in FIG. 5, the batteries 504, 508 can be arranged on one side of patient 12 as opposed to on opposite sides as depicted in FIG. 4. Moreover, FIG. 5 further shows how the battery 508 can be coupled via another coupling 506 to a charging unit 510, which draws electrical power from a standard AC power outlet 512. As described above with respect to the batteries 404, 408, it will be understood that the batteries 504, 508 may each also include both an input and output connector to allow for the modular serial connection described. It will be understood that providing for an extra connection via coupling 506 allows either of batteries 504, 508 to be charged by charging unit 510 during operation of blood pump assembly 14. Moreover, both the batteries 504, 508 can be configured to couple with any number of other power sources including other similarly configured batteries, other charging units configured similarly to the charging unit 510, or other suitable sources of electrical power.

Figure 6:
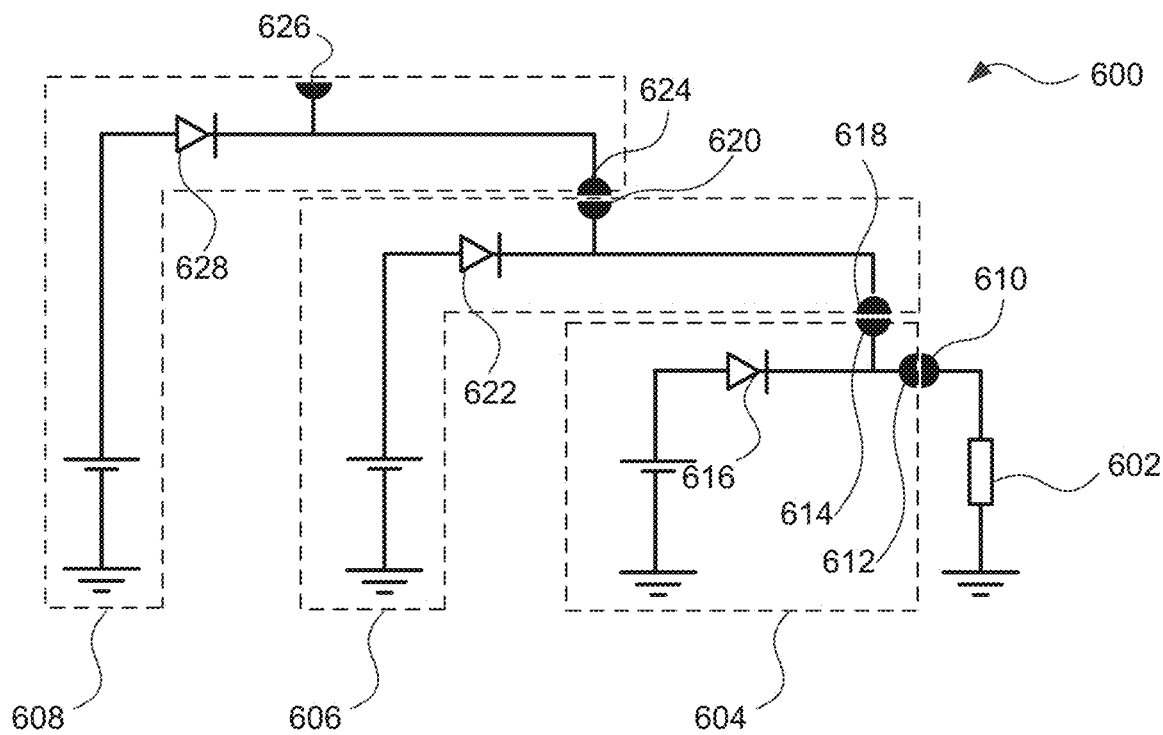
FIG. 6 is a simplified schematic diagram illustrating a modular external power supply system, in accordance with many embodiments.

FIG. 6 is a simplified schematic diagram illustrating an assembly 600 of modular energy storage devices 604, 606, 608 that are mechanically coupled in series and electrically coupled in parallel. The assembly 600 can be employed in employed in any of systems 400 and 500 described above. In the illustrated embodiment, the assembly 600 supplies electrical power to an electrical load 602, which can correspond with an implantable blood pump such as implantable blood pump 14 described above. The electrical power supplied to the electrical load 602 can be supplied by any suitable combination of the modular energy storage devices 604, 606, 608. The modular energy storage devices 604, 606, and 608 can include any of the base modules or batteries described above with respect to FIGS. 4-6, or any other suitable energy storage devices configured to provide electrical power to an implantable blood pump. For example, the modular energy storage device 604 can be a simplified electrical representation of components of the base module 402, 502 including one or more base module battery cells, and the modular energy storage devices 606, 608 can be simplified electrical representations of components of external battery modules 404, 408, 504, 508.

In the illustrated embodiment, the modular energy storage devices 604, 606, 608 each include two connectors, allowing for a daisy-chained connection of the energy storage devices 604, 606, 608. The modular energy storage device 604 includes an output connector 612 and an input connector 614. The output connector 612 couples with a connector 610 to provide electrical power to the implantable blood pump. The input connector 614 is configured to receive electrical power from one or more of the modular energy storage devices 606, 608. Similarly, the modular energy storage device 606 includes an output connector 618 and an input connector 620. The output connector 618 couples with the input connector 614 of the modular energy storage device 604 to provide electrical power to the implantable blood pump and/or the modular energy storage device 604. The input connector 620 is configured to receive electrical power from the modular energy storage device 608. The modular energy storage device 608 similarly includes an output connector 624 and an input connector 626. The output connector 624 couples with input connector 620 of modular energy storage device 606 to provide electrical power to the implantable blood pump, the modular energy storage device 604, and/or the modular energy storage device 606. The input connector 626 is configured to receive electrical power from another source. Although depicted as open in FIG. 6, the input connector 626 can be connected to any suitable electrical power source, including another modular energy storage device with input and output connectors, a charging unit drawing power from a standard AC power outlet, or any other suitable electrical power source. Although each of the modular energy storage devices 606 and 608 are shown as including a grounding element, it will be understood that this may be effectively achieved by including a grounded connection in each input and output connector described above. Thus, input connectors 614, 620, 626 and output connectors 618, 624 may each include both electrical power contacts and ground contacts to couple each component to a grounded connection.

The modular energy storage devices 604, 606, 608 can also include components 616, 622, and 628 for controlling the energy flow in accordance with any desired energy management strategy. For example, as depicted in FIG. 6, the components 616, 622, 628 can be diodes and associated components used to prevent flow of electrical power into a modular energy storage device that has a lower voltage than the other modular energy storage devices. In many embodiments, components 616, 622, 628 may include electronically controlled switches (e.g., metal-oxide-semiconductor field-effect transistors (MOSFETs)) that are used to control distribution of electrical power received via the respective input connector to be output via the respective output connector and used to charge the respective one or more battery cells if not already fully charged.

The assembly 600 allows each successive modular energy storage device to be physically connected in series and electrically connected in parallel. Such an arrangement allows each of the successive modular energy storage devices to provide a redundant source of power to drive the implantable blood pump. For example, if the modular energy storage device 604 is a base module such as base module 402, 502 configured to control implantable blood pump 14 and provide power thereto, and the base module 402, 502 is discharged, either or both of the modular energy storage devices 606, 608 can supply electrical power to the base module 402, 502 to drive implantable blood pump 14 in lieu of base module 402, 502 and/or to charge the battery cells of modular energy storage device 604.

Figure 7:
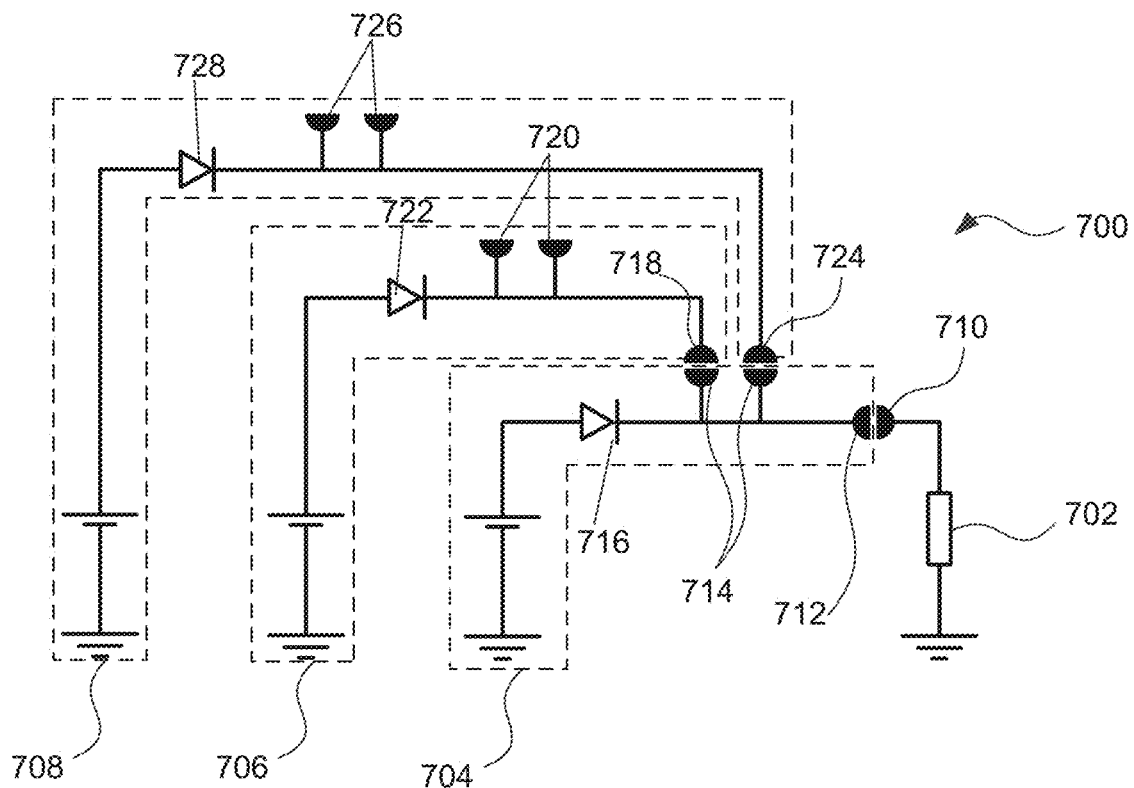
FIG. 7 is a simplified schematic diagram illustrating a modular external power supply system, in accordance with many embodiments.

FIG. 7 is a simplified schematic diagram illustrating an assembly 700 of a modular external power supply system, in accordance with many embodiments. Similar to the assembly 600 described above, the assembly 700 supplies power to an electrical load 702 via any suitable combination of modular energy storage devices 704, 706, 708. The assembly 700 functions similar to assembly 700 described above, except that each of the modular energy storage devices 704, 706, 708 includes two input connectors (714, 720, and 726 respectively). The additional input connectors allow the modular energy storage devices 704, 706, 708 to be connected in branching networks. For example, the modular energy storage device 704 can be connected to the electrical load 702 via an output connector 712 of the device 704. As illustrated, both of the modular energy storage devices 706, 708 can be simultaneously connected to the modular energy storage device 704 via input connectors 714. Accordingly, the modular energy storage devices 706, 708 can be both physically and electrically connected in parallel relative to one another. Relative to the modular energy storage device 704, however, the modular energy storage devices 706, 708 are each physically connected in series and electrically connected in parallel. The modular energy storage devices 706, 708 each have two input connectors 720 and 726 respectively, which are depicted as open connectors and can be connected to any suitable electrical power source, including another modular energy storage device, a charging unit drawing power from a standard AC power outlet, or any other suitable electrical power source. The modular energy storage devices 704, 706, 708 can include components 716, 722, 728 (e.g., diodes or equivalent) that can function the same as the components 616, 622, 628 described above with respect to the assembly 600. As described above with respect to input connectors 614, 620, 626 and output connectors 618, 624, input connectors 714, 720, 726 and output connectors 718, 724 may each include both electrical power contacts and ground contacts to couple each component to a grounded connection.

It will be understood that the systems described above with respect to FIGS. 4-7 allow for increased patient flexibility. Specifically, energy storage modules with the above-referenced mechanical and electrical arrangement and input and output connectors may be designed with limited capacity since any number of such energy storage modules may be connected to the system to provide sources of power to drive an implantable blood pump. For example, the individual energy storage modules may each provide an average runtime (depending on the load) of one to two hours, and accordingly may be designed to be more compact and less cumbersome than typical battery packs used to power VADs. Systems with this modularity may still provide around-the-clock battery support, since any number of batteries may be mechanically coupled in series and electrically coupled in parallel. Thus, patients can choose to bring a number of batteries that will provide adequate run time depending on the patient's intended activity. For example, when planning a short errand, the patient may bring a single energy storage module. If, for example, the patient will be away from home all day, the patient may bring and/or couple more batteries to the system. This modularity can allow the patient to carry less weight on most days, and the weight that is carried may be better distributed due to the compact nature of the batteries.

Figure 8A:
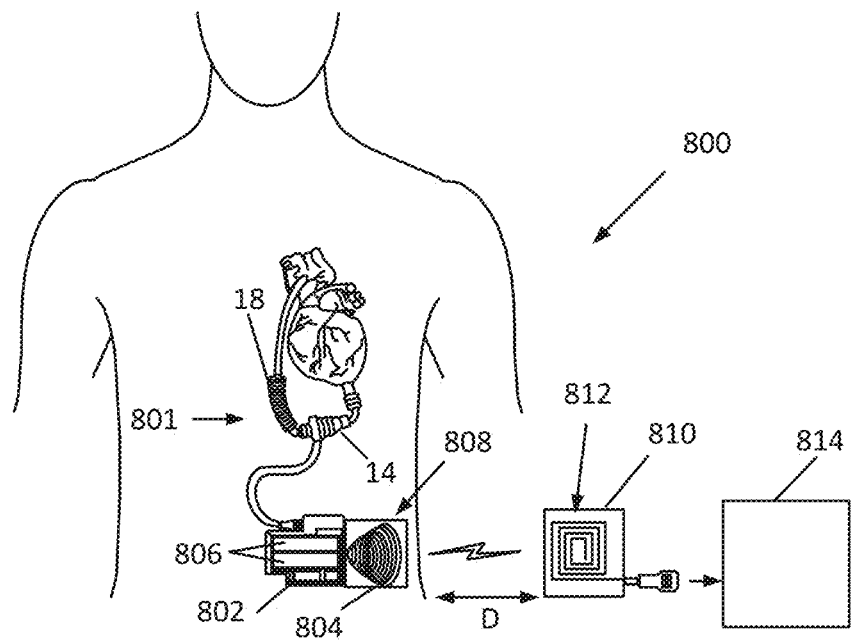
FIG. 8A illustrates a mechanical circulatory support system with a Transcutaneous Energy Transfer System (TETS) implanted in a patient's body in a first position, in accordance with many embodiments.
Figure 8B:
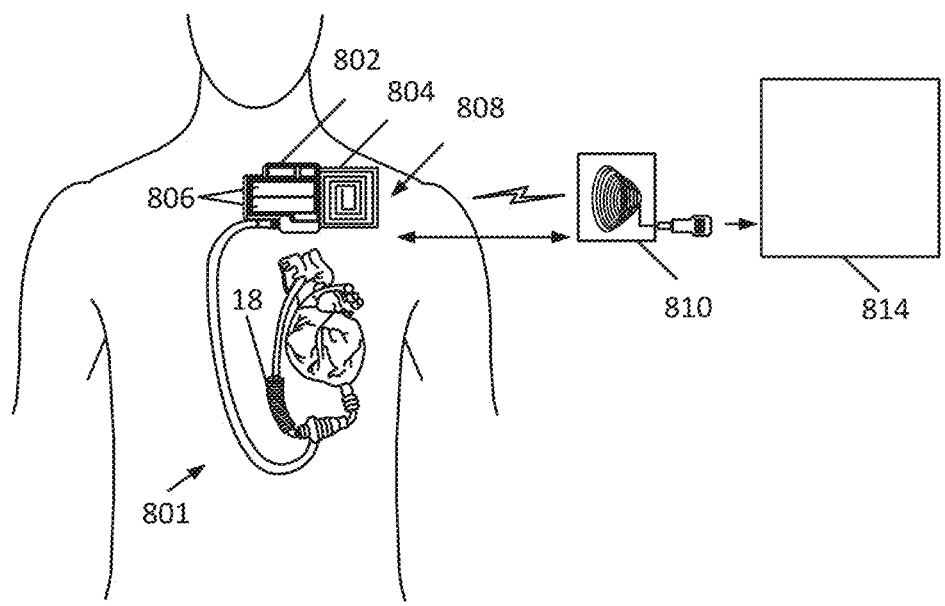
FIG. 8B illustrates a mechanical circulatory support system with a Transcutaneous Energy Transfer System (TETS) implanted in a patient's body in a second position, in accordance with many embodiments.

Although the systems described above have primarily been directed to external power supply systems that provide power to an implantable blood pump by a driveline cable that enters the patient's body through the abdomen, similar systems and approaches can be applied to systems that provide power to an implantable blood pump wirelessly via transcutaneous energy transfer. FIGS. 8A and 8B illustrate exemplary embodiments of a mechanical circulatory support system 800 with a transcutaneous energy transfer system (TETS) implanted in a patient's body. System 800 includes internal components 801 including a cannula 18, a blood pump 14, a rechargeable power storage device 802, also referred to herein as an implantable power supply 802, and a power receiver unit 804. The rechargeable power storage device 802 can include two or more energy storage components 806, which can be, for example, batteries including rechargeable batteries, capacitors, fuel cells, or the like.

The rechargeable power storage device 802 can be implanted in a location away from the cannula 18, for example, in the lower abdominal as shown in FIG. 8A. The power receiving unit 804 includes a TETS receiver 808 that can be, for example, a receiver, a resonator, and inductive coil or the like, that can be coupled to the power storage device 802, which is the electrical load of the power receiver unit 804.

The mechanical circulatory support system 800 also includes a power transmitter unit 810, that is external to the patient. In accordance with many embodiments, the transmitter unit 810 can be configured similarly to any of the base modules described above with respect to power supplied via serially-connected external battery modules. The transmitter unit 810 includes a transmitter resonator 812, also referred to herein as a TETS transmitter 812. The transmitter resonator 812 can include, for example, a coil, including an inductive coil that is configured to be coupled to an electric power source 814 such as an electrical wall outlet or external power sources. When the transmitter unit 810 is powered by, for example, connection to the electric power source 814, an electrical current is generated in the coil of the transmitter resonator 812.

The transmitter resonator 812 as part of the transmitter unit 810 can be embedded in a stationary object such as a wall, a chair, a bed, or other fixtures such as a car seat or objects that do not move by themselves without external control or human assistance. The source of power for a stationary and embedded transmitter resonator is generally alternating current from an electric outlet, but can also be direct current from a battery source. In other embodiments, the transmitter resonator 812 may be part of a piece of wearable clothing such as a vest or a jacket, or other wearable accessories. In the case of a transmitter resonator that is embedded into a piece of clothing or object wearable by a person that moves with a person, the source of power can be portable sized rechargeable batteries that also could be worn by the patient as described below with respect to FIG. 9.

When the receiver unit 804 in the patient comes within a separation distance D of the transmitter unit 810, the mechanical circulatory support system 800 is able to wirelessly transfer energy from the transmitter unit 810 to the receiver unit 804 to recharge the power storage device 802 of the internal components 801. In one embodiment, at a given separation distance D being in the range of 2.5 cm to 35 cm, the transmitter unit 810 is able to deliver power in the range of 5 W to 20 W to the receiver unit 804 to recharge the batteries 806 in the power storage device 802 of the internal components 801.

Figure 9:
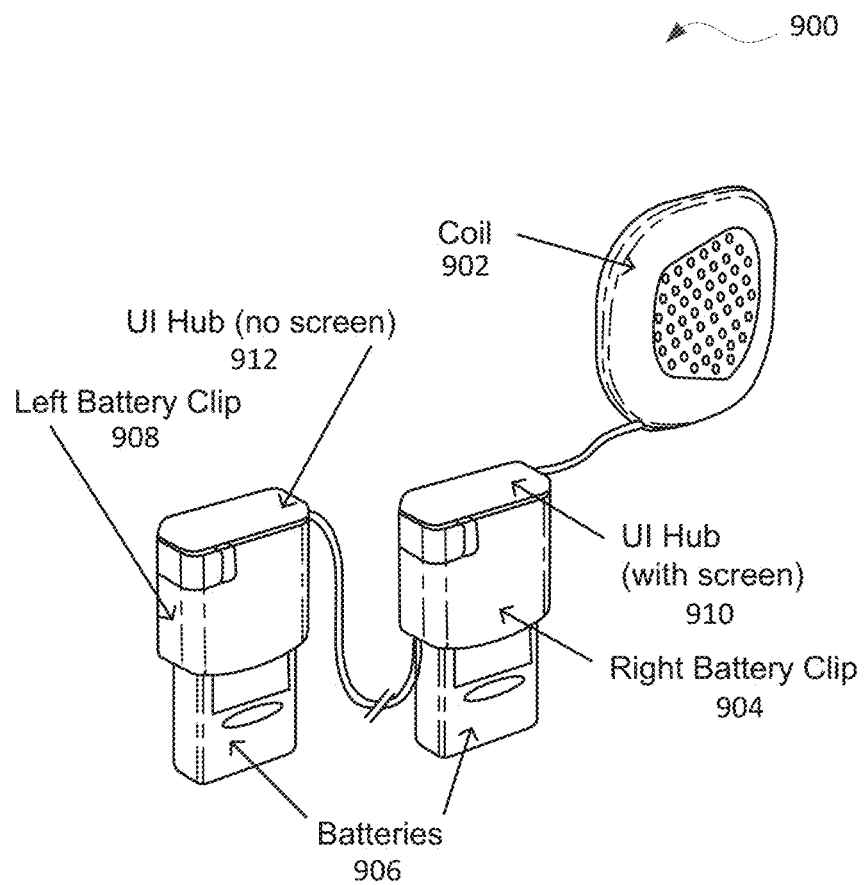
FIG. 9 illustrates components of a modular external power supply system that may be employed with the Transcutaneous Energy System (TETS) depicted in FIG. 8A or 8B, in accordance with many embodiments.

The electric power source 814 can include any arrangement of the serially-connectable modular energy storage modules described herein. FIG. 9 shows components 900 of a modular external power supply system that can be employed with the Transcutaneous Energy System (TETS) depicted in FIGS. 8A and 8B. As shown in FIG. 9, the components 900 include a coil 902 that can correspond to the inductive coil of transmitter resonator 912 described above. The coil 902 can be coupled to a right battery clip 904, which is configured to hold a first battery 906. The components 900 further include a left battery clip 908, which is physically connected to right battery clip 904 and configured to hold a second battery 906. In many embodiments, the batteries 906 are mechanically connected in series and electrically connected in parallel so as to provide redundant sources of power to drive the implantable blood pump. In some embodiments, the right battery clip 904 includes a user interface (UI) hub 910 with a screen configured to display charge status of one or more of the batteries 906. The left battery clip 908 can include a UI hub 912 with or without a screen and be configured to display charge status of the battery 906 held by the left battery clip 908. Although not shown in FIG. 9, the left battery clip 908 can further include an input connector configured to allow additional power sources to be coupled thereto, including additional batteries 906, a charging unit drawing power from a standard AC power outlet, or any other suitable electrical power source.

Figure 10:
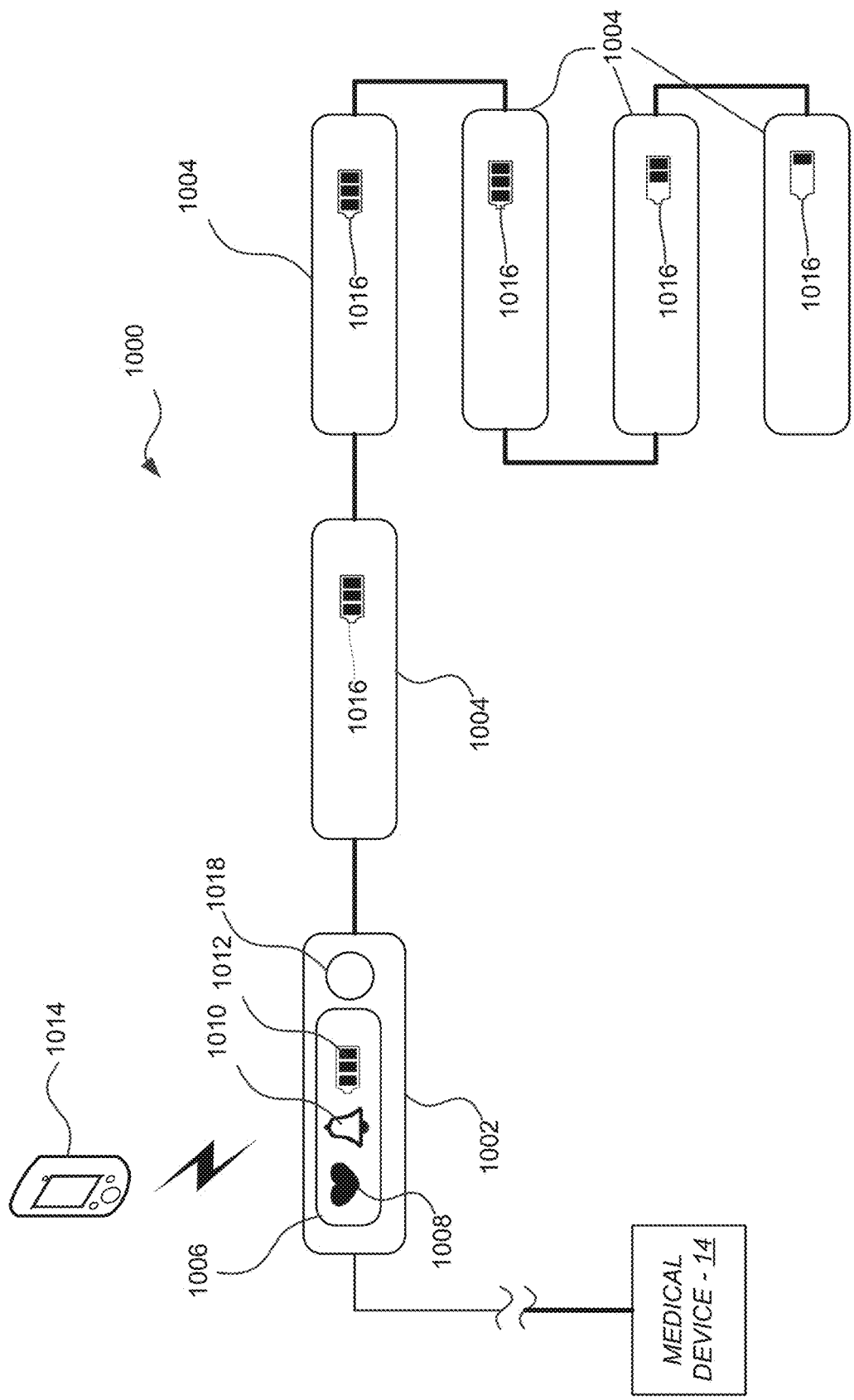
FIG. 10 illustrates indicators that may be employed in a modular external power supply system, in accordance with many embodiments.

FIG. 10 is a simplified illustration of indicators that can be employed in a modular external power supply system 1000. The system 1000 can include a base module 1002, which can correspond with any of the base modules described above, and which can be coupled via a driveline or wirelessly to a medical device 14, which can correspond to the implantable blood pump 14 as described herein. The system 1000 can also include a number of modular energy storage devices 1004 mechanically coupled in series and electrically coupled in parallel as described herein. The base module 1002 includes a display 1006 with indicators 1008, 1010, 1012. A heart-shaped indicator 1008 can provide a high priority indication that a major failure of the system is occurring and may alert the user to seek immediate assistance and/or support. For example, the heart-shaped indicator 1008 can be displayed when components of medical device 14 are malfunctioning such that operation of the implantable blood pump is severely impaired or stopped entirely. The bell-shaped indicator 1010 can provide a lower priority indication related to the available power capacity of the system 1000. For example, the bell-shaped indicator 1010 can flash yellow when one or more batteries reaches a first threshold of depletion, and can flash red when one or more batteries reaches a second increased threshold of depletion. The battery-shaped indicator 1012 can provide additional detail as to the specific level of charge of batteries of the system 1000. The display 1006 can include a number of battery-shaped indicators 1012 that can provide indications as to the level of charge of batteries within base module 1002 or any of modular energy storage devices 1004 coupled thereto.

Any of the indications provided on the display 1006 can be wirelessly transmitted to a mobile device 1014. Indications may be given on the mobile device 1014 in any suitable manner, including by notification messages or displayed indicators similar to those on display 1006 within applications on the mobile device 1014. In some embodiments, other operating information of system 1000 or any components thereof can be transmitted wirelessly to be displayed on mobile device 1014. In addition to the visual indicators described above, base module 1002 can be configured to provide audio indicators. For example, the base module 1002 can include a speaker (not shown) configured to beep with a particular pattern and/or tone to indicate malfunctions with the system 1000 and/or particular levels of power remaining. The base module 1002 can also include a user input button 1018, which can be configured to allow a user to silence any of the aforementioned audio indicators. For example, in some embodiments, if a beeping alert regarding the power of the batteries of base module 1002 is sounded, a user can press input button 1018 once to silence the alert.

In addition to the indicators described above, each of the modular energy storage devices 1004 can include indicators 1016 that display the level of charge of each respective modular energy storage device 1004. The indicators 1016 can include LEDs, which can be segmented to display one or more levels of charge associated with the respective energy storage device 1004. In some embodiments, the segments associated particular levels of charge can have different colors of light to provide a further indication of the level of charge. For example, the LED in the rightmost segment of indicator 1016 associated with the highest level of charge can be green, an intermediate segment associated with an intermediate level of charge can be yellow, and the leftmost segment associated with the lowest level of charge can be red.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for supplying power to an implantable blood pump, the system comprising:
   a base module operatively coupled with the implantable blood pump to supply electrical power to drive the implantable blood pump, wherein the base module comprises a base module input connector;
   a first modular energy storage device comprising one or more first modular energy storage device battery cells, a first modular energy storage device input connector, and a first modular energy storage device output connector; wherein the first modular energy storage device output connector is configured for selective coupling with the base module input connector to supply electrical power to the base module; and
   a second modular energy storage device comprising one or more second modular energy storage device battery cells, a second modular energy storage device input connector, and a second modular energy storage device output connector; wherein the second modular energy storage device output connector is configured for selective coupling with the first modular energy storage device input connector to supply electrical power to the first modular energy storage device, wherein the first and second modular energy storage devices are configured to provide redundant sources of power to drive the implantable blood pump, and wherein the one or more first modular energy storage device battery cells and the first modular energy storage device input connector are connected so that the one or more first modular energy storage device battery cells and the one or more second modular energy storage device battery cells are connected in parallel via coupling of the second modular energy storage device output connector with the first modular energy storage device input connector.

2. The system of claim 1, wherein the first modular energy storage device output connector is configured to be releasably coupled with the base module input connector, and wherein the second modular energy storage device output connector is configured to be releasably coupled with the first modular energy storage device input connector.

3. The system of claim 1, further comprising a third modular energy storage device comprising one or more third modular energy storage device battery cells, a third modular energy storage device input connector, and a third modular energy storage device output connector; wherein the third modular energy storage device output connector is configured for selective coupling with the second modular energy storage device input connector, wherein the third modular energy storage device is configured to provide an additional redundant source of power to drive the implantable blood pump, and wherein the one or more second modular energy storage device battery cells and the second modular energy storage device input connector are connected so that the one or more second modular energy storage device battery cells and the one or more third modular energy storage device battery cells are connected in parallel via coupling of the third modular energy storage device output connector with the second modular energy storage device input connector.

4. The system of claim 1, wherein the first modular energy storage device and the second modular energy storage device are interchangeable.

5. The system of claim 1, wherein the first modular energy storage device and the second modular energy storage device are identical.

6. The system of claim 1, wherein the base module comprises a controller coupled to the implantable blood pump, the controller comprising an internal energy storage device configured to provide power to drive the implantable blood pump, wherein the first or second modular energy storage devices are configured to provide power to drive the implantable blood pump when the internal energy storage device is in a depleted state.

7. The system of claim 6, wherein the base module comprises a controller that is configured to power the implantable blood pump through a driveline cable.

8. The system of claim 6, wherein the base module comprises an external energy transmitter that powers the implantable blood pump wirelessly by transcutaneous energy transmission.

9. The system of claim 1, further comprising a charging unit coupled with the second modular energy storage device input connector, wherein the charging unit draws power from an AC power outlet.

10. The system of claim 1, wherein each of the first and second modular energy storage devices and the base module are configured to be worn externally by a patient implanted with the implantable blood pump.

11. The system of claim 1, wherein the base module comprises one or more indicators configured to indicate a level of power available to drive the implantable blood pump or a fault associated with the implantable blood pump.

12. The system of claim 11, wherein the one or more indicators comprise visual indicators.

13. The system of claim 11, wherein the base module is configured to wirelessly transmit one or more notifications regarding the level of power available to drive the implantable blood pump or the fault to an external device.

14. The system of claim 1, wherein the first modular energy storage device comprises electronically controlled switches that are operable to control distribution of electrical power received via the first modular energy storage device input connector between output via the first modular energy storage device output connector and charging of the first modular energy storage device battery cells.

15. A modular external electrical power system for supplying power to an implantable blood pump, the system comprising:
a first modular energy storage device comprising one or more first modular energy storage device battery cells, a first modular energy storage device input connector, and a first modular energy storage device output connector; wherein the first modular energy storage device output connector is operatively configured to supply electrical power to drive the implantable blood pump, and wherein the one or more first modular energy storage device battery cells and the first modular energy storage device input connector are connected so that the one or more first modular energy storage device battery cells and one or more second modular energy storage device battery cells connected to the first modular energy storage device input connector are connected in parallel, and wherein the first modular energy storage device input connector is configured to accommodate selective coupling of the one or more second modular energy storage device battery cells with the first modular energy storage device input connector.

16. The system of claim 15, wherein the first modular energy storage device comprises a control unit configured to drive the implantable blood pump.

17. The system of claim 15, further comprising a second modular energy storage device comprising the one or more second modular energy storage device battery cells, a second modular energy storage device input connector, and a second modular energy storage device output connector.

18. The system of claim 17, wherein the first modular energy storage device and the second modular energy storage device are interchangeable.

19. The system of claim 17, wherein the first modular energy storage device and the second modular energy storage device are identical.

20. The system of claim 17, further comprising a charging unit connected to the second modular energy storage device input connector, wherein the charging unit draws power from an AC power outlet.

21. The system of claim 17, wherein the first and second modular energy storage devices are configured to be worn externally by a patient.

* * * * *